(12) United States Patent
Kosaka (10) Patent No.: US 6,670,885 B2
(45) Date of Patent: Dec. 30, 2003

(54) DRUG ADMINISTERING SYSTEM AND ADMINISTERING METHOD

(75) Inventor: Hiroyuki Kosaka, Okayama (JP)

(73) Assignee: Gansui Kaihatsu Corporation, Okayama (JP)

( * ) Notice: Subject to any disclaimer, the term of this patent is extended or adjusted under 35 U.S.C. 154(b) by 0 days.

(21) Appl. No.: 10/049,339

(22) PCT Filed: Jun. 7, 2001

(86) PCT No.: PCT/JP01/04821
§ 371 (c)(1),
(2), (4) Date: Jun. 11, 2002

(87) PCT Pub. No.: WO01/97113
PCT Pub. Date: Dec. 20, 2001

(65) Prior Publication Data
US 2002/0163435 A1 Nov. 7, 2002

(51) Int. Cl.[7] ............................................. G08B 1/00
(52) U.S. Cl. ................... 340/309.15; 340/506; 340/3.1; 340/505; 705/2; 705/3; 700/233
(58) Field of Search .................. 340/506, 3.1, 505, 340/286.02, 286.07; 700/233, 236; 705/2, 3

(56) References Cited

U.S. PATENT DOCUMENTS 6,202,923 B1 * 3/2001 Boyer et al. ................. 235/375
6,421,650 B1 * 7/2002 Goetz et al. .................... 705/3
6,542,902 B2 * 4/2003 Dulong et al. ............ 707/104.1
6,578,003 B1 * 6/2003 Camarda et al. ................ 705/3

FOREIGN PATENT DOCUMENTS

| JP | 6-292657 | 10/1994 |
|---|---|---|
| JP | 8-115376 | 5/1996 |
| JP | 9-182780 | 7/1997 |
| JP | 9-094287 | 8/1997 |
| JP | 9-225008 | 9/1997 |
| JP | 9-253163 | 9/1997 |
| JP | 11-066213 | 9/1999 |
| JP | 2001-155098 | 6/2001 |

* cited by examiner

Primary Examiner—Daryl Pope
(74) Attorney, Agent, or Firm—Webb Ziesenheim Logsdon Orkin & Hanson, P.C.

(57) ABSTRACT

A medication system prevents medication mistake by checking kinds and doses of pharmaceuticals, coincidence of patient, and so on, when a doctor forms a clinical chart, when a pharmacist prepares the pharmaceuticals following the clinical chart or when the prepared pharmaceuticals are medicated to the patient. Patient barcodes showing the kinds and doses of the pharmaceuticals to be medicated are affixed on the clinical chart when the pharmacist prepares the pharmaceuticals, the barcodes provided on a receptacle or a package of the pharmaceuticals are read by a barcode reader and contents are compared by accessing a database in a server by a second terminal equipment. Furthermore, a patient barcode provided in the vicinity of a bed of an inpatient is read by a portable terminal equipment; the patient barcodes are compared to be judged whether the patients coincide or not.

24 Claims, 5 Drawing Sheets

DRUG ADMINISTERING SYSTEM AND ADMINISTERING METHOD

TECHNICAL FIELD

The present invention relates to a medication system and a medication method for medicating pharmaceuticals to patients in a medical field such as a hospital by which erroneous medication can be prevented.

BACKGROUND ART

When pharmaceuticals are medicated to patients in a hospital or in a pharmacy, a pharmacist or a nurse (hereinafter, called "medical attendant") mixes pharmaceuticals or takes out predetermined kinds and numbers of merchandized pharmaceuticals from a cabinet by following a prescription or a clinical chart of a doctor, and the packed pharmaceuticals are given to patients. Alternatively, the pharmaceuticals are medicated to inpatients by injection or instillation at a predetermined time interval.

Generally, a lot of kinds of the pharmaceuticals are treated in the hospital or the pharmacy, and some of the appearances of the packages of the pharmaceuticals or the shapes of tablets are similar to each other. Thus, a certain degree of knowledge and carrier with respect to of the pharmaceuticals is necessary for selecting the designated pharmaceuticals in the prescription or the clinical chart among the many pharmaceuticals, precisely. Especially, due to the increase of the kinds of the pharmaceuticals, busyness in the medical field, a small number of medical attendants by rationalization of the hospital administration, or the like, it cannot be denied that different kind or dose of the pharmaceuticals designated in the prescription or the clinical chart is given to the patient due to the error of the medical attendant. Furthermore, it cannot be denied that the pharmaceuticals for other person is medicated to a patient due to the missing of the patients.

When erroneous kind or dose of pharmaceutical is medicated to a patient or the patient is mistaken, the erroneous pharmaceuticals directly injures patient's life. For preventing the mistake of the kind and dose of the pharmaceuticals, mental burden of the medical attendant becomes larger. Furthermore, when a system checking the kind and dose of the pharmaceuticals by a plurality of persons for preventing the medication mistake, personnel and economical burden will be increased.

On the other hand, catalogues inserting pharmaceutical information is conventionally published for the medical attendants. Since the dose of the pharmaceutical information inserted in the catalogue is too large, it cannot be denied that a doctor erroneously combines the pharmaceuticals never be combined or misses the dose of the pharmaceuticals when the doctor describes the prescription or the clinical chart. At that case, the prescription or the clinical chart inherently has errors, so that it is impossible to prevent the medication mistakes even though the pharmaceuticals are strictly checked at the medication.

DISCLOSURE OF INVENTION

The present invention is objected to solve the above-mentioned problems of the prior art, and to provide a medication system and a medication method of the pharmaceuticals in which it is possible to check whether the kind and the dose of the pharmaceuticals are followed the prescription or the clinical chart or not, whether the pharmaceuticals and the patient to be medicated coincide with those of the prescription or the clinical chart or not when the pharmaceuticals is medicated to the patient. Furthermore, the present invention is objected to provide a medication system and a medication method of the pharmaceuticals in which the pharmaceuticals never be combined and the dose of the pharmaceuticals can be checked when the doctor describes the prescription or the clinical chart.

For achieving the above-mentioned objects, a medication system of pharmaceuticals in accordance with the present invention comprises: a database for memorizing kinds of pharmaceuticals and information with respect to each pharmaceutical; a first recognition means connected to the database and for recognizing at least the kind and dose of a pharmaceutical from a distinguishing mark provided on a receptacle or a package of each pharmaceutical; a second recognition means connected to the database and for recognizing at least the kind and dose of pharmaceutical from a distinguishing mark provided on a prescription or a clinical chart; a comparison means for comparing the kinds and doses of the pharmaceuticals recognized by the first recognition means with those recognized by the second recognition means; and an alarm means for outputting an alarm when at least one of the kinds and the doses of pharmaceuticals does not coincide in a result of the comparison by the comparison means.

Another medication system of pharmaceuticals in accordance with the present invention comprises: a first database for memorizing kinds of pharmaceuticals and information with respect to each pharmaceutical; a second database for memorizing prescriptions or clinical charts on which information with respect to kinds and doses of pharmaceuticals medicated to patients are electronically recorded; a first recognition means connected to the first database and for recognizing at least the kind and dose of a pharmaceutical from a distinguishing mark provided on a receptacle or a package of each pharmaceutical; a clinical chart reading means connected to the second database, for accessing the second database based on an information for identifying a patient and for reading an inherent electronic prescription or clinical chart of the patient; a second recognition means for recognizing at least the kind and dose of pharmaceutical from the electronic prescription or clinical chart; a comparison means for comparing the kinds and doses of the pharmaceuticals recognized by the first recognition means with those recognized by the second recognition means; and an alarm means for outputting an alarm when at least one of the kinds and the doses of pharmaceuticals does not coincide in a result of the comparison by the comparison means.

On the other hand, a medication method of pharmaceuticals in accordance with the present invention is characterized by including the steps of: memorizing kinds of pharmaceuticals and information with respect to each pharmaceutical in a database; providing a distinguishing mark corresponding to the kind and a dose of each pharmaceutical on a receptacle or a package thereof; providing a distinguishing mark corresponding to kinds and doses of pharmaceuticals described on a prescription or a clinical chart to the prescription or clinical chart; reading the distinguishing mark provided on the prescription or clinical chat by using a recognition apparatus when pharmaceuticals to be medicated to a patient are prepared by following the description of the prescription or clinical chart; reading the distinguishing mark provided on the receptacle or package of the prepared pharmaceuticals by using the recognition apparatus; comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

Another medication method of pharmaceuticals in accordance with the present invention is characterized by including the steps of: memorizing kinds of pharmaceuticals and information with respect to each pharmaceutical and electronic prescriptions or clinical charts, on which at least kinds and doses of pharmaceuticals to be medicated to patients are described, in a database; providing a distinguishing mark corresponding to kind and dose of pharmaceutical on a receptacle or a package thereof; reading the distinguishing mark provided on the receptacle or package of the prepared pharmaceuticals by using a recognition apparatus when the pharmaceuticals to be medicated to a patient are prepared by following the kinds and doses of the pharmaceuticals described on the electronic prescription or clinical chart; comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

BEST MODE FOR CARRYING OUT THE INVENTION

Figure 1:
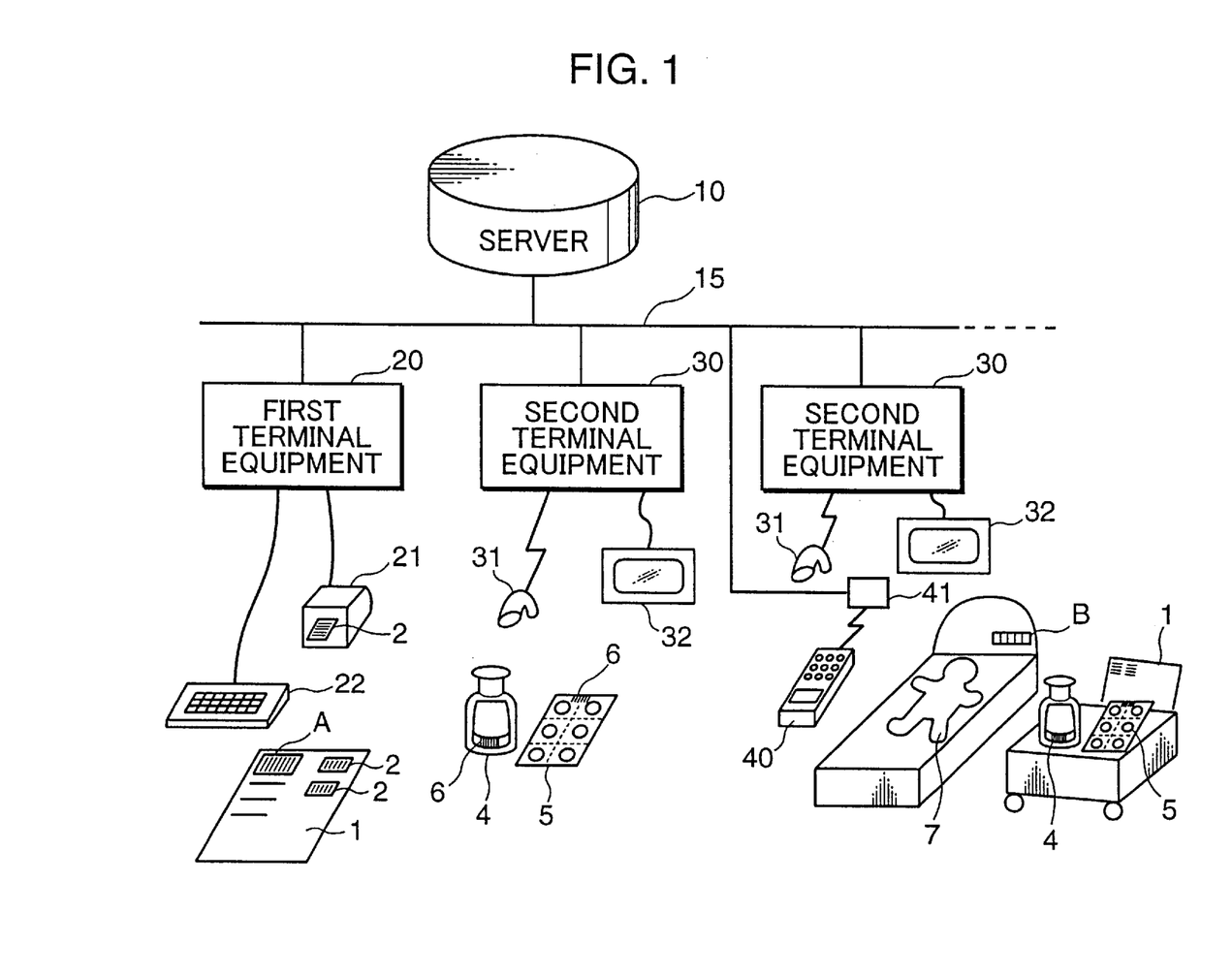
FIG. 1 is a block diagram for showing a configuration of a medication system of pharmaceuticals in an embodiment of the present invention.

An embodiment of a medication system and a medication method of pharmaceuticals in accordance with the present invention is described. A block configuration of the medication system in the embodiment is shown in FIG. 1.

A first terminal equipment 20 is provided, for example, in a dispensary of a doctor, and a printer 21, a key board 22, and so on are connected thereto. A plurality of second terminal equipments 30 respectively having substantially the same configuration are provided, for example, in a pharmacy, nurse rooms, and so on in a hospital, and a barcode reader 31, a monitor display 32, and so on are connected to each second terminal equipment 30. A third terminal equipment 40 is, for example, a cordless portable terminal equipment which can be carried by a medical attendant, and has functions of the barcode reader, the computer, and so on. It is possible to provide a receiver 41 for connecting the third terminal equipment 40 to a server 10 through a network 15 in each patient's room, if necessary.

The terminal equipments 20, 30 and 40 are respectively connected to the server 10 through the network 15. In case that this system is used in one hospital, a LAN (local area network) is used as the network 15 for connecting the server 10 and the terminal equipments 20, 30 and 40. Alternatively, in case that this system is used in a plurality of hospitals, the server 10 is provided on a web, and the terminal equipments 20, 30 and 40 are connected to the server 10 through an internet using a public network such as a telephone line or ISDN (integrated services digital network) or a dedicated line.

When a doctor examines a patient and decides kinds and doses of pharmaceuticals which are effective to remedy the patient, he inputs the name of the patient, names of the pharmaceuticals and the doses of the pharmaceuticals, and so on through the key board 22. When the names of the pharmaceuticals and so on are inputted, the first terminal equipment 20 accesses information with respect to the pharmaceuticals (hereinafter, it is called "database") which is memorized in the server 10 through the network 15, and reads codes corresponding to the kinds and medication doses of the inputted pharmaceuticals from the database. The codes read from the database are printed as distinguishing marks such as barcodes by the printer 21 (hereinafter, the distinguishing mark is called "barcode"). The barcodes 2 are affixed on a prescription or clinical chart 1. A patient barcode "A" is similarly printed by the printer 21 and affixed on the prescription or clinical chart 1. These operations can be operated by another medical attendant by following the instruction of the doctor.

When the prescription or clinical chart 1 is carried to a nurse room, a medical attendant reads the barcodes 2 and the patient barcode "A" affixed on the prescription or clinical chart 1 by using the barcode reader 31. The second terminal equipment 30 accesses the database in the server 10 with using information of the barcodes 2 and the patient barcode "A", and reads the kinds and doses of the pharmaceuticals indicated by the barcodes 2 from the server 10. The data read from the server 10 is memorized in an internal memory and displays on the monitor display 32. The intended use of the patient barcode "A" will be described below.

On the other hand, the medical attendant takes instructed numbers or doses of instructed pharmaceuticals from a medicine cabinet in which the pharmaceuticals are classified with reading the kinds and doses of the pharmaceuticals from the prescription or clinical chart 1 written by characters or with watching the information displayed on the monitor display 32. Furthermore, it is assumed that the administration of the pharmaceuticals can be automated by a machine in the future, the pharmaceuticals instructed by the doctor will automatically be taken by the instructed numbers or doses.

Subsequently, the medical attendant reads barcodes 6 which is printed or affixed on a receptacle 4 (when the pharmaceuticals is liquid type, the receptacle is an ample, a vial, or the like) or a package 5 (when the pharmaceuticals is tablet or capsule type, the receptacle is a PTP (press through package), or the like) of the pharmaceuticals by using the barcode reader 31. The second terminal equipment 30 accesses the information with respect to the pharmaceuticals memorized in the server 10 with using the information of the barcodes 6, and reads the kinds, doses, methods of medication (oral inoculation, injection, instillation, suppository, and so on) of the pharmaceuticals specified by the barcodes 6 from the database in the server 10. The data read from the database is memorized in the internal memory and displayed on the monitor display 32.

Furthermore, the second terminal equipment 30 compares the information with respect to the kinds and doses of the pharmaceuticals obtained with using the barcodes 2 affixed on the prescription or clinical chart 1 with those obtained with using the barcodes 6 on the receptacles 4 or the packages 5 of the pharmaceuticals, and judges whether they coincide with each other or not. When at least one of the kinds and the doses of the pharmaceuticals does not coincide, the second terminal equipment 30 outputs an alarm (or warning) via a speaker, or the like. As a result, the medical attendant can understand that the prepared pharmaceuticals are different from the instruction by the doctor. In that case, the pharmaceuticals are re-prepared, so that it is possible to prevent the medication mistake that the different kinds and/or doses of the pharmaceuticals from the instruction by the doctor will be medicated to the patient.

When the kinds and the doses of the pharmaceuticals coincide with those described on the prescription or clinical chart 1, the medical attendant carries the prepared pharmaceuticals, for example, to an inpatient 7, and the pharmaceuticals will be medicated to the inpatient 7. Thus, the third terminal equipment 40 is connected to the second terminal equipment 30 for memorizing the contents such as the patient barcode "A" affixed on the prescription or clinical chart 1 for identifying the patient read by the barcode reader 31, the method for medicating the pharmaceuticals, and so on into the third terminal equipment 40.

On the other hand, a patient barcode "B" for identifying the inpatient 7 is provided on the body of the inpatient 7 or in the vicinity of a bed. The medical attendant reads both of the patient barcode "A" affixed on the prescription or clinical chart 1 and the patient barcode "B" provided, for example, in the vicinity of the bed by using the third terminal equipment 40. The third terminal equipment 40 judges whether the patient recognized by the patient barcode "B" coincides with that by the patient barcode "A" or not. When the patients identified by the patient barcodes "A" and "B" do not coincide with each other, the third terminal equipment 40 outputs an alarm (or a warming) via an integrated speaker, or the like. As a result, the medical attendant can understand that the prepared pharmaceuticals are erroneously carried to another patient, so that it is possible to prevent the medication mistake that the pharmaceuticals for another patient will erroneously be medicated to the different patient. Alternatively, when the patients identified by the patient barcodes "A" and "B" coincide with each other, the medical attendant medicates the pharmaceuticals to the inpatient 7 following the steps instructed in the prescription or clinical chart 1.

As the information with respect to the pharmaceuticals memorized in the server 10, name, capability information whether it can be medicated with another pharmaceuticals or not, permissible dose in each medication or in a predetermined time period, an elapsed time between the medications, medication method, existence for allowing the medication and notice with respect to each pharmaceutical are recited.

As well known, each pharmaceutical has some adverse reaction, so that life or health of the patient will be damaged by adverse affect of the pharmaceuticals when a plurality of kinds of pharmaceuticals are medicated at the same time. Thus, specific pharmaceuticals are prohibited to be combined with another pharmaceuticals. In an actual problem, it is impossible that the doctor checks all the pharmaceuticals which are prohibited to be combined with another pharmaceuticals with respect to a lot of kinds of pharmaceuticals. Thus, it cannot be denied that two or more kinds of pharmaceuticals which are prohibited to be combined with each other will be medicated.

Thus, it is possible to configure the system in a manner so that it judges whether the pharmaceuticals prohibited to be combined with another pharmaceuticals are contained in two or more pharmaceuticals inputted by the doctor with using the information with respect to the pharmaceuticals memorized in the server 10. In such the case, when the kinds of the pharmaceuticals are inputted through the key board 22, the first terminal equipment 20 accesses to the database in the server 10, reads the capability information whether it can be medicated with another pharmaceuticals or not with respect to each inputted pharmaceuticals, and judges the capability of each pharmaceutical with other pharmaceuticals. When the pharmaceuticals prohibited to be combined with another pharmaceuticals is included, the first terminal equipment 20 outputs an alarm via the speaker, or the like. By such the modification in which the combination of the pharmaceuticals is automatically checked by the first terminal equipment 20 when the barcodes 2 corresponding to the kinds and doses of the pharmaceuticals are affixed on the prescription or clinical chart 1, it is possible to prevent the medication of the pharmaceuticals which are prohibited to be combined with each other. Furthermore, it is possible to configure the system in a manner so that the kinds and total doses of the pharmaceuticals which had been medicated to each patient, time of the medication, and so on are memorized in the database in the server 10, and the first terminal equipment 20 judges not only the capability of each pharmaceutical with respect to another pharmaceuticals to be medicated at this time, but also the capability of each pharmaceutical with respect to the pharmaceuticals medicated to the patient in the past.

Furthermore, as well known, a dose at each medication, a total dose in a predetermined time period, a medication prohibit time period between the medications, and so on are decided with respect to each pharmaceutical for prohibiting the surplus medication of the pharmaceuticals. Thus, it is possible to configure the system in a manner so that a data memory region with respect to each patient is provided in the database in the server 10 for memorizing the kinds of the pharmaceuticals, total doses and dates and times of medications of each pharmaceutical medicated to the patient. It is possible to judge whether the dose of the pharmaceuticals at one medication is surpassed a permissible dose or not, whether the total dose of each pharmaceutical in a predetermined time period is surpassed a permissible total dose or not, and whether the elapsed time from the last medication to this medication reaches to the medication prohibit time period (predetermined time period) or not. In case that the dose at one medication is surpassed the permissible dose, the alarm is outputted by the speaker, or the like at the time when the prescription or clinical chart 1 is described. In case that the total dose of each pharmaceutical is surpassed the permissible total dose or the elapsed time between the medications has not been reached the medication prohibit time period, the alarm is outputted by the speaker, or the like at the time when the medical attendant prepares the pharmaceuticals to be medicated to the patient.

In the latter case, the dose of each pharmaceutical is accumulatively memorized in the memory region of each patient in the database with the access date (including the time), when the second terminal equipment 30 accesses the database in the server 10. When the second terminal equipment 30 accesses the database in the server 10 at next time, the second terminal equipment judges whether the total dose of each pharmaceutical in the predetermined time period surpasses the permissible total dose or not and whether the elapsed time from the last medication reaches to the medication prohibit time period or not.

It is possible to use the date and time when the patient barcode "B" provided in the vicinity of the bed is read by the third terminal equipment 40 as the date and time of the medication of the pharmaceuticals instead of the time when the second terminal equipment 30 accesses the database in the server 10. In such the case, the receiver 41 transmits the date and time when the third terminal equipment 40 reads the patient barcode "B" to the server 10.

Figure 2:
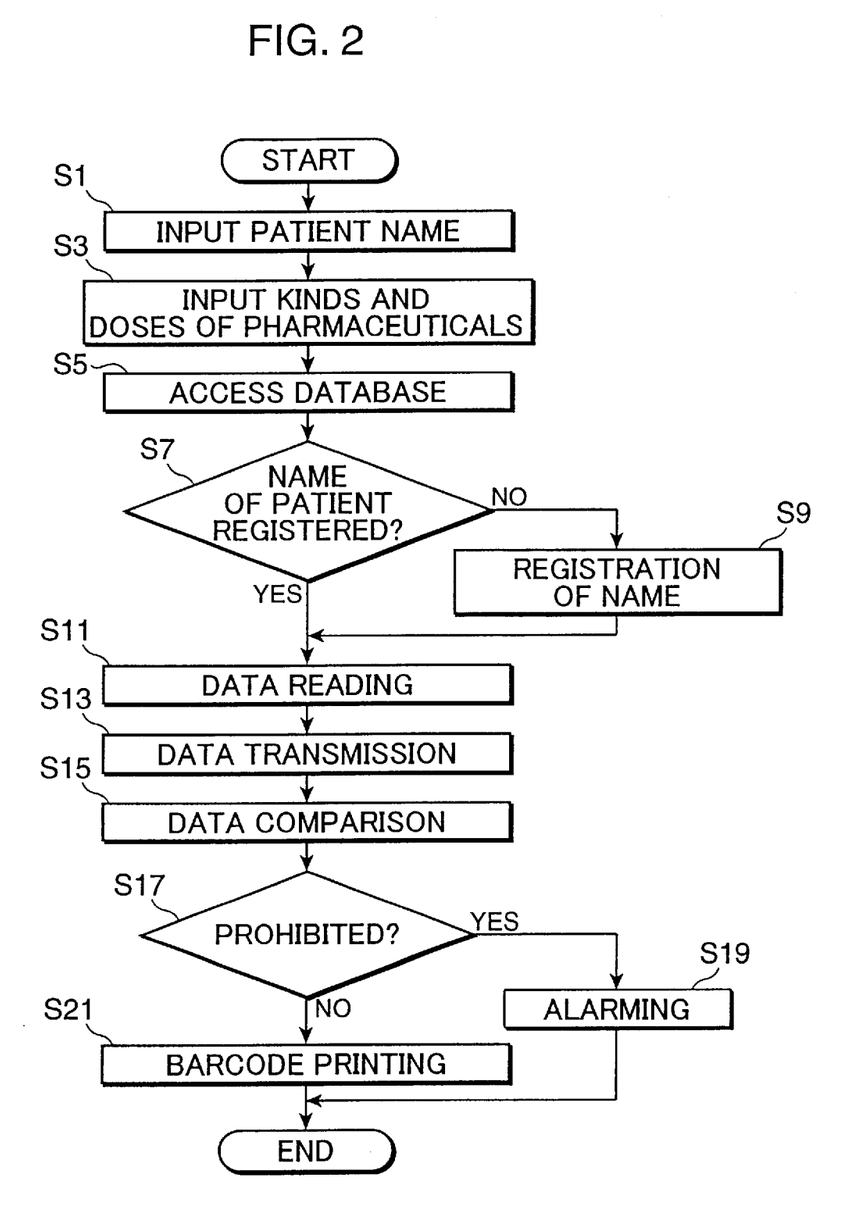
FIG. 2 is a flowchart for showing steps when a doctor describes a prescription or a clinical chart in the embodiment.

Subsequently, processes for printing the barcodes with respect to the kinds and doses of the pharmaceuticals to be affixed on the prescription or clinical chart by the doctor is described with reference to a flowchart shown in FIG. 2.

The doctor inputs name of the patient through the key board 22 (Step S1), and inputs the kinds and doses of the pharmaceuticals to be medicated to the patient (Step S3). When these data are inputted, the first terminal equipment 20 accesses the database in the server 15 via the network 15 with using the data (Step S5).

When the server 10 receives an access signal from the first terminal equipment 20, it judges whether the name of the patient has been registered or not (Step S7). When the name of the patient has not been registered, the name of the patient is registered and a dedicated memory region for the patient is assigned in the database (Step S9). Alternatively, when the name of the patient has been registered, the database is accessed for reading the data with respect to the pharmaceuticals corresponding to the access signals (Step S11), and the data is transmitted to the first terminal equipment 20 (Step S13).

The first terminal equipment 20 compares the data transmitted from the server 10 (Step S15), and judges whether two or more pharmaceuticals which are prohibited to be combined with each other are included in the pharmaceuticals instructed by the doctor or not and whether the dose of each pharmaceutical is equal to or smaller than the permissible dose or not (Step S17).

Hereupon, when the pharmaceuticals prohibited to be combined with each other are included or when the dose of at least one pharmaceuticals is surpasses the permissible dose, the first terminal equipment 20 outputs the alarm by using the buzzer, or the like (Step S19), and completes the operation. Alternatively, when the pharmaceuticals prohibited to be combined with each other are not included (NO in Step S17), the first terminal equipment 20 prints the barcodes 2 corresponding to the kinds and doses of the pharmaceuticals and the patient barcode "A" for identifying the patient by using the printer 21 (Step S21), and completes the operation.

Figure 3:
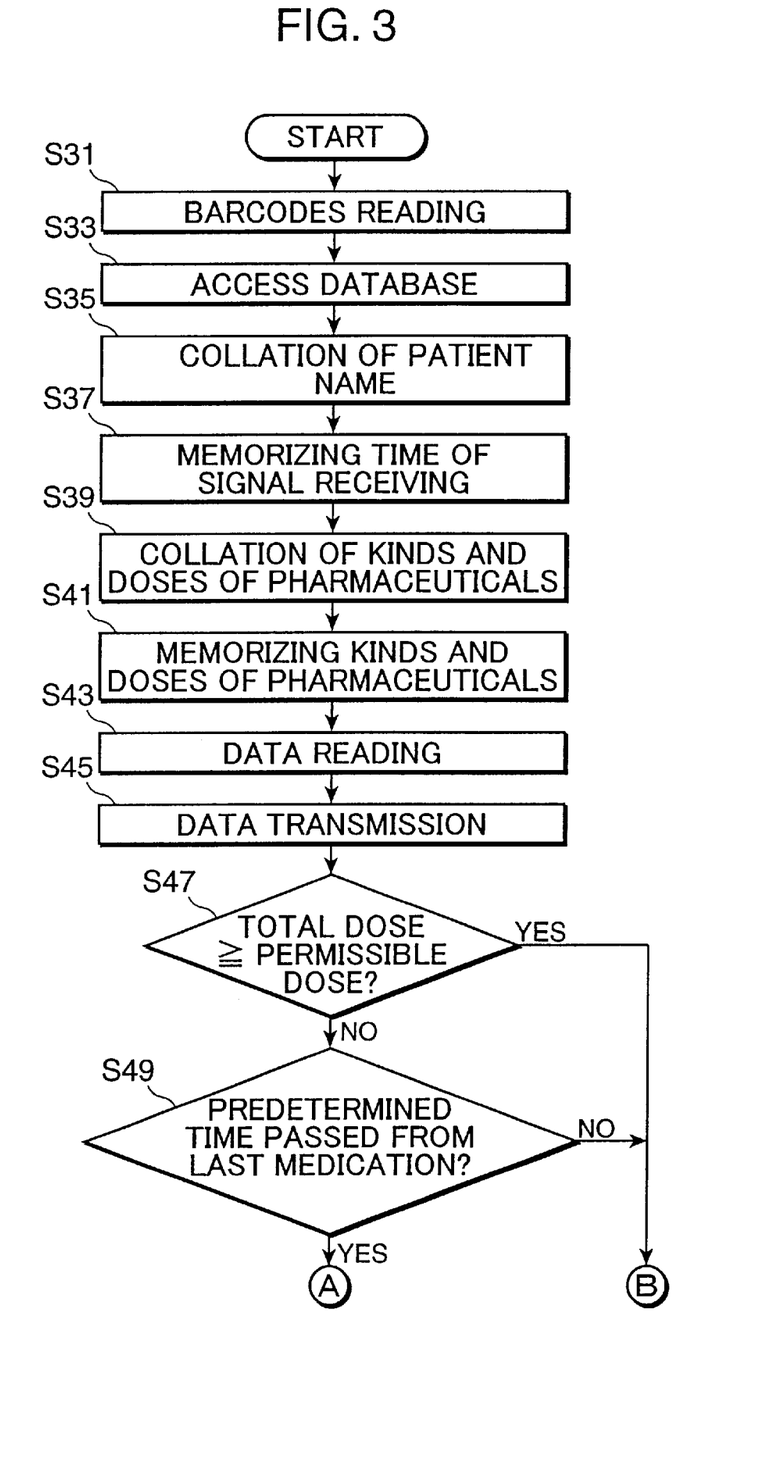
FIG. 3 is a flowchart for showing steps when a medical attendant prepares pharmaceuticals to be medicated to a patient by following instruction of the prescription or clinical chart in the embodiment.
Figure 4:
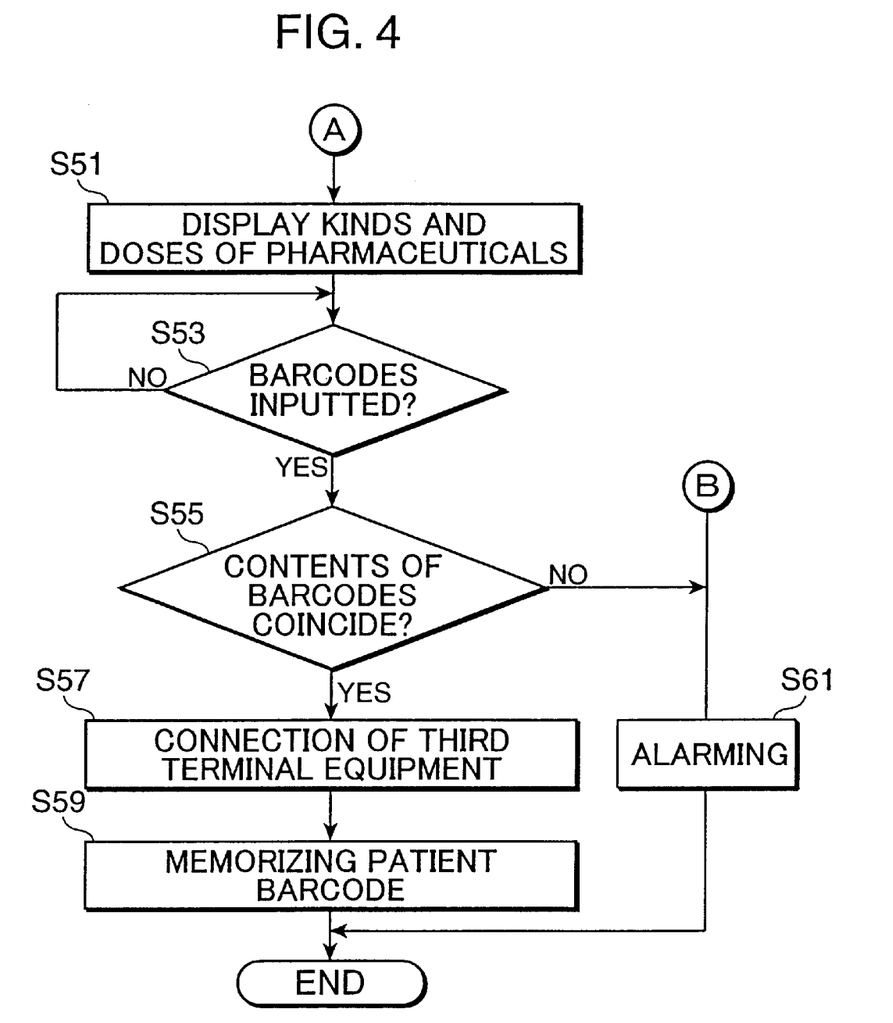
FIG. 4 is a flowchart for showing the continued portion of the flow in FIG. 3.

Subsequently, processes for preparing the pharmaceuticals to be medicated to a patient by the medical attendant following to the prescription or clinical chart written by the doctor in the pharmacy or nurse room is described with reference to a flowchart shown in FIGS. 3 and 4.

When the medical attendant uses the barcode reader 31 for reading the patient barcode "A" and the barcodes 2 showing the kinds and doses of the pharmaceuticals affixed on the prescription or clinical chart 1 (Step S31), the second terminal equipment 30 accesses the database in the server 10 via the network 15 with using the data corresponding to the barcodes (Step S33).

When the server 10 receives the access signals from the second terminal equipment 30, it collates the name of the patient (Step S35), and memorizes the time of receiving the access signals into a memory region dedicated to the patient (Step S37). Subsequently, the server 10 collates the kinds of the pharmaceuticals included in the access signals. When the kind of the pharmaceuticals is new, the server 10 registers the kind of the pharmaceuticals and memorizes the dose. Alternatively, when the kind of the pharmaceuticals has been registered, the server 10 memorizes the dose of the pharmaceuticals accumulatively on the total dose thereof (Step S41). Furthermore, the server 10 reads the data with respect to the kinds of the pharmaceuticals with respect to the patient corresponding to the access signals (Step S43), and transmits the data to the second terminal equipment 30 (Step S45).

The second terminal equipment 30 reads the data transmitted from the server 10, and judges whether the total dose of each pharmaceutical in a predetermined time period including the dose at this time surpasses the permissible total dose or not (Step S47). When the total dose does not surpass the permissible total dose (NO in Step S47), the second terminal equipment 30 further judges whether the elapsed time from the last medication to this medication surpasses the medication prohibit time period (predetermined time) or not (Step S49).

When the elapsed time surpasses the predetermined time, the pharmaceuticals have no problem even though they are medicated to the patient, so that the second terminal equipment 30 displays the kinds and doses of the pharmaceuticals instructed in the prescription or clinical chart on the monitor display 32 (Step S51). When the administration of the pharmaceuticals will be automated by the machine in the future, the data read from the database will directly be outputted to the administration machine of the pharmaceuticals.

Subsequently, the second terminal equipment 30 waits that the medical attendant takes the instructed numbers or doses of the pharmaceuticals from the medicine cabinet with reference to the description of the prescription or clinical chart 1 or the information displayed on the monitor display 32, and the barcodes printed or affixed on the receptacle 4 or package 5 of all the prepared pharmaceuticals by using the barcode reader 31 (Step S53).

When the barcodes 6 on the receptacle 4 or the package 5 of the pharmaceuticals are read, the second terminal equipment 30 judges whether the contents of the barcodes 6 coincide with the contents of the barcodes 2 affixed on the prescription or clinical chart 1 (Step S55). Hereupon, when the barcodes 2 and the barcodes 6 adopt the same system, the second terminal equipment 30 can be judged whether they coincide with each other or not without accessing the server 10 again. On the other hand, when the barcode system of the merchandized pharmaceuticals is used as the barcodes 6 as it is, the second terminal equipment 30 accesses the information with respect to the pharmaceuticals memorized in the server 10 with using the information of the barcodes 6, reads the kinds and doses of the specified pharmaceuticals by the barcodes 6, and judges whether the contents of the barcodes 6 coincide with the contents of the barcodes 2 or not with using the data.

When the contents of the barcode 6 coincide with the contents of the barcodes 2, the kinds and doses of the pharmaceuticals prepared by the medical attendant coincide with the those described on the prescription or clinical chart 1, so that the pharmaceuticals will be medicated to the inpatient 7. Thus, the third terminal equipment 40 is connected to the second terminal equipment 30 for memorizing the contents of the patient barcode "A" read by the barcode reader 31 into the third terminal equipment 40 (Step S59), and complete the operation.

On the other hand, when the total dose in the predetermined time surpasses the permissible total dose in step S47, when the elapsed time from the last medication to this medication does not surpass the medication prohibit time period (predetermined time) in step S49, and when the contents of the barcodes 6 does not coincide with the contents of the barcodes 2 in step S55, that is, the kinds and doses of the prepared pharmaceuticals do not coincide with the kinds and doses of the pharmaceuticals described on the prescription or clinical chart 1, the pharmaceuticals should not be medicated to the patient. The second terminal equipment 30 outputs an alarm (or a warning) by the speaker or the like (Step S61), and completes the operation.

Figure 5:
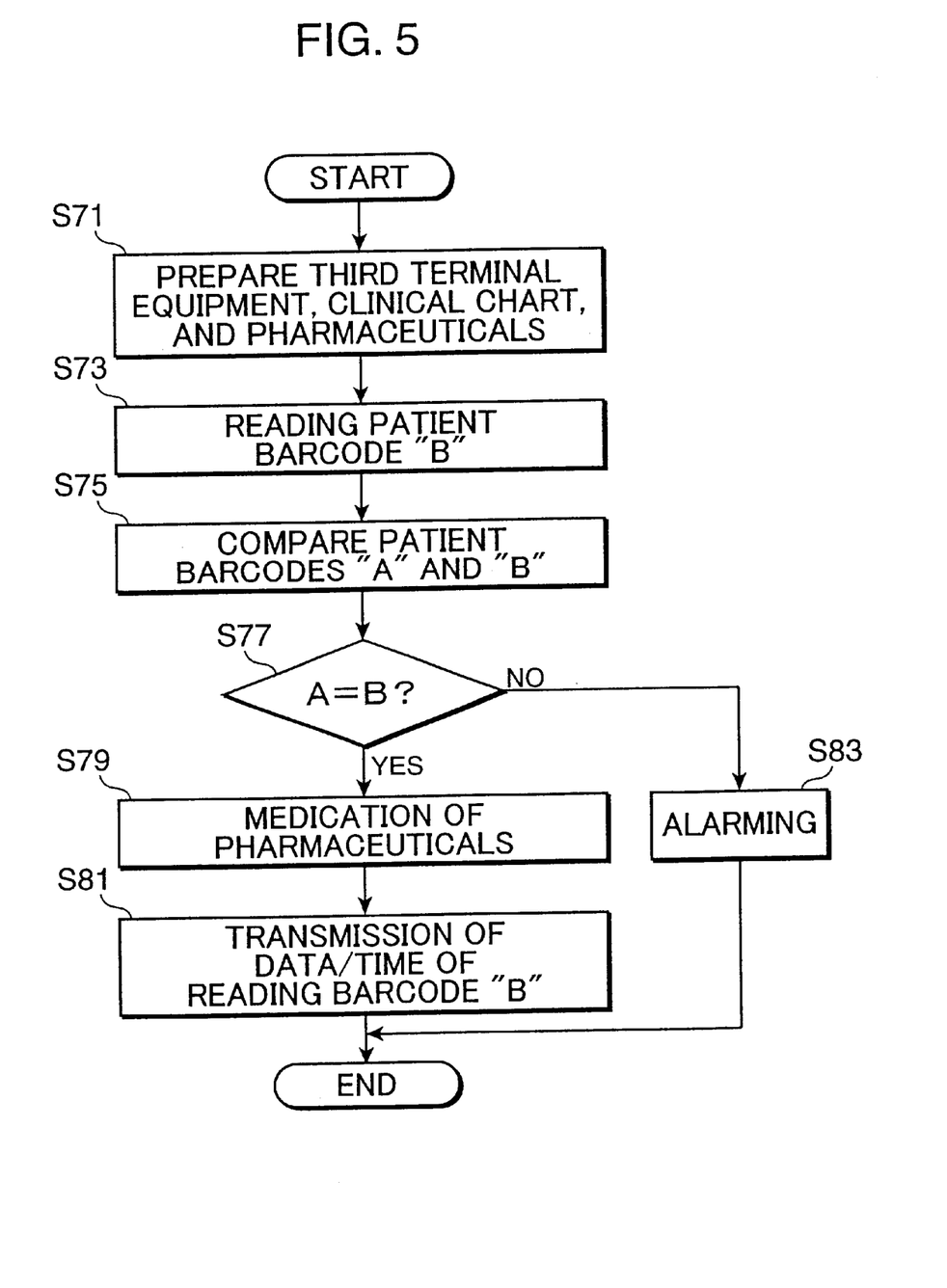
FIG. 5 is a flowchart for showing steps when the medical attendant actually medicates the pharmaceuticals to the patient in the embodiment.

Subsequently, processes for medicating the prepared pharmaceuticals to the patient following to the prescription or clinical chart 1 by the medical attendant is described with reference to a flowchart shown in FIG. 5.

At first, the medical attendant goes to the patient room for medicating the pharmaceuticals to the inpatient 7 with carrying the third terminal equipment 30 memorizing the patient barcode "A", the prescription or clinical chart 1 by the doctor and the pharmaceuticals (Step S71). When the medical attendant reaches to the patient room, the patient barcode "B" provided on the body of the inpatient 7 or in the vicinity of the bed is read by a barcode reader in the third terminal equipment 40 (Step S73).

When the patient barcode "B" is read, the third terminal equipment 40 compares the read barcode "B" with the previously memorized patient barcode "A" (Step S75), and judges whether they coincide with each other or not (Step S77). When the patient barcode "B" coincides with the patient barcode "A" (YES in Step S77), the inpatient 7 coincides the patient described on the prescription or clinical chart 1, so that the medical attendant medicates the prepared pharmaceuticals to the inpatient 7 following the instruction of the prescription or clinical chart 1 (Step S79). Furthermore, the third terminal equipment 40 transmits the date and time when the patient barcode "B" is read to the receiver 41, if necessary (Step S81), and completes the operation.

On the other hand, when the patient barcode "B" does not coincide with the patient barcode "A" (NO in Step S77), the inpatient 7 is another person from the patient described on the prescription or clinical chart 1, so that the prepared pharmaceuticals may not be medicated to the inpatient 7. The third terminal equipment 40 outputs an alarm by the speaker, or the like (Step S83), and completes the operation.

Subsequently, another modification of medication system of pharmaceuticals in the embodiment is described. The matters which are not described in the following are substantially the same as those in the above-mentioned embodiment, so that the explanation of them are omitted.

In the above-mentioned embodiment, the system is configured for accessing the database in the server 10 via the network 15 by using the terminal equipments 20, 30 and 40 having the computer function. Thus, it is possible to form the prescription or clinical chart with respect to each patient as an electronic information (hereinafter, it is called "electronic clinical chart"), the electronic clinical charts are memorized in a second database in the server 10 or another server, and the electronic clinical chart in the second database is read by the terminal equipments 20, 30 and 40 as occasion demands.

When the doctor inputs the name of the patient through the key board 22, the first terminal equipment 20 accesses the electronic clinical chart of the patient in the second database in the server 10 via the network 15, reads the electronic clinical chart of the patient and displays it on the monitor display (not shown in the figure). Subsequently, when the doctor examines the patient and decides the kinds and doses of the pharmaceuticals which are effective to remedy the patient, he inputs the name of the patient, the names and doses of the pharmaceuticals, and so on through the key board 22. When the names of the pharmaceuticals, and so on are inputted, the first terminal equipment 20 accesses the first database in the server 10 via the network 15 for reading the information corresponding to the kinds and doses of the inputted pharmaceuticals. The information read from the database are taken into the electronic clinical chart displayed on the monitor display, and memorized as a part of the contents of the electronic clinical chart. It is possible to configure the system to judge whether two or more pharmaceuticals prohibited to be combined with each other are included in the inputted pharmaceuticals by the doctor or not, and whether the dose of each pharmaceutical at one time surpasses the permissible dose or not, at this stage.

When the examination is completed, the doctor memorizes the electronic clinical chart into the second database in the server 10 via the network 15 from the first terminal equipment 20. The copies of the electronic clinical charts are transmitted to the second terminal equipment 30 in the pharmacy or the nurse room. When the second terminal equipment 30 receives the electronic clinical chart from the first terminal equipment 20, it signs that the electronic clinical chart is received by a sound information, or the like to the medical attendant, and displays the contents of the electronic clinical chart on the monitor display 32.

The medical attendant takes instructed numbers or doses of instructed pharmaceuticals from the medicine cabinet in which the pharmaceuticals are classified with watching the electronic clinical chart displayed on the monitor display 32, and reads the barcodes 6 on a receptacle 4 or a package 5 of the pharmaceuticals by using the barcode reader 31. The second terminal equipment 30 accesses the first data base in the server 10 with using the information of the barcodes 6, and reads the kinds, doses, methods of medication (oral inoculation, injection, instillation, suppository, and so on) of the pharmaceuticals specified by the barcodes 6 from the first database in the server 10. The data read from the database is memorized in the internal memory and displayed on the monitor display 32.

Furthermore, the second terminal equipment 30 compares the information with respect to the kinds and the doses of the pharmaceuticals described on the electronic clinical chart with those obtained with using the barcodes 6 on the receptacles 4 or the packages 5 of the pharmaceuticals, and judges whether they coincide with each other or not. When at least one of the kinds and the doses of the pharmaceuticals does not coincide, the second terminal equipment 30 outputs an alarm (or warning) via a speaker, or the like. On the other hand, when the kinds and the doses of the pharmaceuticals coincide with those described on the prescription or clinical chart 1 (SIC: correctly, it should be "electronic clinical chart"), the medical attendant carries the prepared pharmaceuticals, for example, to an inpatient 7, and the pharmaceuticals will be medicated to the inpatient 7. Thus, the third terminal equipment 40 is connected to the second terminal equipment 30 for memorizing the contents such as the information with respect to the patient and the method for medicating the pharmaceuticals, and so on into the third terminal equipment 40.

The medical attendant reached to the inpatient 7 reads the patient barcode "B" provided on the body of the patient or in the vicinity of the bed by using the third terminal equipment 40. The third terminal equipment 40 compares the patient information memorized in the memory with the information of the patient barcode "B", and judges whether the patient coincides or not.

By the above-mentioned modification, the clinical chart which has conventionally been described on a paper and exchanged between the doctor and the medical attendant is formed as the electronic information, so that the data can be transmitted between the terminal equipments. Thus, the medical services can be executed smoothly. Furthermore, the medical treatment can be checked at each stage, so that the medication mistake can be prevented. It is possible to configure the system in a manner so that the second database with respect to inherent patients of the electronic prescription or clinical chart is stored in a server such as a personal computer provided in each hospital, and the first database with respect to the pharmaceuticals is stored in the server on the web.

As mentioned above, the medication system and the medication method of the pharmaceuticals in accordance with the present invention checks: (1) whether the pharmaceuticals prohibited to be combined with another pharmaceuticals are included in the pharmaceuticals selected by the doctor or not; (2) whether the dose of each pharmaceutical surpasses the permissible dose or not; (3) whether the kinds and doses of the pharmaceuticals prepared by the medical attendant coincide with those instructed in the prescription or clinical chart or not; (4) whether the total dose of each pharmaceutical of each patient surpasses the permissible total dose or not; (5) whether the elapsed time from the last medication to this medication with respect to each pharmaceutical of each patient surpasses the medication prohibit time period or not; and (6) the inpatient 7 to be medicated the pharmaceuticals coincides with the patient identified in the prescription or clinical chart 1 or not, at respective stages. Thus, the phytotoxicity due to the medication mistake can be prevented.

The term "pharmaceuticals" in the above-mentioned description of the embodiment includes all the ones used in the medical field such as the instillation for supplying nutrition, poultice, and so on further to the medicine for remedy the patient. Furthermore, the barcodes are used for identifying the patient in the above-mentioned embodiment, but it is not restricted by the description. The patient can be identified with using his cornea or fingerprint, if possible.

Furthermore, the database memorizing the information with respect to the pharmaceuticals in the server 10 is not especially explained in the above-mentioned embodiment. It, however, is possible to form the database for each hospital or for a group of related hospitals. Alternatively, it is possible to use the databases disclosed by a manufacturer of the pharmaceuticals, an association of the manufacturers, or a national agency.

Furthermore, the barcodes are used as the distinguishing marks in the above-mentioned embodiment, but it is not restricted by the barcode. It is possible to use two-dimensional barcodes, symbols, or other distinguishing marks can be used. When the symbols are used, it can be read by the OCR (optical characteristic reader).

INDUSTRIAL APPLICABILITY

As mentioned above, the medication system of pharmaceuticals in accordance with the present invention comprises: a database for memorizing kinds of pharmaceuticals and information with respect to each pharmaceutical; a first recognition means connected to the database and for recognizing at least the kind and dose of a pharmaceutical from a distinguishing mark affixed on a receptacle or a package of each pharmaceutical; a second recognition means connected to the database and for recognizing at least the kind and dose of pharmaceutical from a distinguishing mark affixed on a prescription or a clinical chart; a comparison means for comparing the kinds and doses of the pharmaceuticals recognized by the first recognition means with those recognized by the second recognition means; and an alarm means for outputting an alarm when at least one of the kinds and the doses of pharmaceuticals does not coincide in a result of the comparison by the comparison means.

That is, when the medical attendant prepares the pharmaceuticals following to the instruction on the prescription or clinical chart by the doctor, the distinguishing mark such as the barcode provided on a receptacle or a package of each prepared pharmaceutical is read by the first recognition means such as the barcode reader. Since the first recognition means is connected to the database, the medical attendant can know the kinds and doses of the prepared pharmaceuticals from the information memorized in the database. Similarly, the distinguishing marks such as the barcodes provided on the prescription or clinical chart for instructing the kinds and doses of the pharmaceuticals are read by the second recognition means such as the barcode reader. The comparison means such as the computer connected to the barcode reader compares whether the kinds and doses of the prepared pharmaceuticals coincide with those instructed on the prescription or clinical chart or not, and outputs an alarm by the alarm means such as the alarming buzzer when they do not coincide with each other. Thus, even when the medical attendant erroneously prepares the kinds and/or doses of the pharmaceuticals, the mistake can be found and alarmed. As a result, the mistake for medicating the erroneous kind and/or doses of the pharmaceuticals to the patient can be prevented. Furthermore, even when the medical attendant has poor knowledge and/or experiences, he can feel easy to execute the medical treatment, so that the mental burden of the medical attendant can be reduced.

Furthermore, another medication system of pharmaceuticals in accordance with the present invention comprises: a first database for memorizing kinds of pharmaceuticals and information with respect to each pharmaceutical; a second database for memorizing prescriptions or clinical charts on which information with respect to kinds and doses of pharmaceuticals medicated to patients are electronically recorded; a first recognition means connected to the first database and for recognizing at least the kind and dose of a pharmaceutical from a distinguishing mark affixed on a receptacle or a package of each pharmaceutical; a clinical chart reading means connected to the second database, for accessing the second database based on an information for identifying a patient and for reading an inherent electronic prescription or clinical chart of the patient; a second recognition means for recognizing at least the kind and dose of pharmaceutical from the electronic prescription or clinical chart; a comparison means for comparing the kinds and doses of the pharmaceuticals recognized by the first recognition means with those recognized by the second recognition means; and an alarm means for outputting an alarm when at least one of the kinds and the doses of pharmaceuticals does not coincide in a result of the comparison by the comparison means.

That is, by such the configuration, the clinical chart which has conventionally been described on a paper and exchanged between the doctor and the medical attendant is formed as the electronic information and the data can be transmitted between the terminal equipments, so that the medical services can be executed effectively, further to the above-mentioned effects. Furthermore, there is no need to affix the barcodes with respect to the patient and the pharmaceuticals on the prescription or clinical chart, so that the time for identifying the patient and the pharmaceuticals can be shortened.

Furthermore, it is possible to prevent the medication mistake due to the erroneous instruction on the prescription or clinical chart by the doctor by configuring the above-mentioned systems in a manner so that the comparison means further judges whether two or more pharmaceuticals are prohibited to be combined with each other when two or more pharmaceuticals has been described or will be described on the prescription or clinical chart; and the alarm means outputs an alarm when two or more pharmaceuticals are prohibited to be combined with each other.

Still furthermore, it is possible to prevent the medication mistake due to the erroneous instruction on the prescription or clinical chart by the doctor or due to the misunderstand of the medical attendant by configuring the above-mentioned systems in a manner so that the second recognition means identifies the patient from the distinguishing marks for identifying the patient provided on the prescription or clinical chart; the first recognition means accumulatively memorizes total dose of each medicated pharmaceutical with respect to each patient identified by the second recognition means in the database; the comparison means compares the total dose of each pharmaceutical with a permissible dose thereof which is previously memorized in the database; and the alarm means outputs an alarm when the total dose surpasses the permissible dose.

Still furthermore, it is possible to prevent the medication mistake due to the erroneous instruction on the prescription or clinical chart by the doctor or due to the misunderstand of the medical attendant by configuring the above-mentioned systems in a manner so that the second recognition means identifies the patient from the distinguishing marks for identifying the patient provided on the prescription or clinical chart; the first recognition means memorizes date and time of last medication of each pharmaceutical with respect to each patient identified by the second recognition means in the database; the comparison means calculates elapsed time from the last medication with respect to each pharmaceutical, and compares the calculated elapsed time with a predetermined time during which the medication is prohibited; and the alarm means outputs an alarm when the elapsed time has not reached to the predetermined time.

Still furthermore, it is possible to prevent the medication mistake that the pharmaceuticals for another patient is erroneously medicated to different patient by configuring the above-mentioned systems in a manner so that a third recognition means is further comprised for recognizing the patient from the patient recognizing mark provided on a body of the patient or in the vicinity of a bed; the comparison means compares the patient recognized by the second recognition means with the patient recognized by the third recognition means; and the alarm means outputs an alarm when the patients do not coincide.

Still furthermore, it is possible to utilize an information with respect to new pharmaceuticals easily when the new pharmaceuticals are developed by configuring the above-mentioned systems in a manner so that the database is memorized in a server connected via a network.

Still furthermore, by configuring at least the third recognition means as a codeless terminal equipment, each medical attendant can carry the codeless terminal equipment and check the pharmaceuticals repeatedly, so that the possibility of occurrence of the medication mistake can be reduced as smaller as possible.

On the other hand, the medication method of pharmaceuticals in accordance with the present invention is characterized by including the steps of: memorizing kinds of pharmaceuticals and information with respect to each pharmaceutical in a database; providing a distinguishing mark corresponding to the kind and a dose of each pharmaceutical on a receptacle or a package thereof; providing a distinguishing mark corresponding to kinds and doses of pharmaceuticals described on a prescription or a clinical chart to the prescription or clinical chart; reading the distinguishing mark provided on the prescription or clinical chat by using a recognition apparatus when pharmaceuticals to be medicated to a patient are prepared by following the description of the prescription or clinical chart; reading the distinguishing mark provided on the receptacle or package of the prepared pharmaceuticals by using the recognition apparatus; comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

That is, when the medical attendant prepares the pharmaceuticals, he confirms whether the kinds and doses of the pharmaceuticals described on the prescription or clinical chart formed by the doctor with those of the pharmaceuticals which are actually prepared by the medical attendant or not with using the distinguishing marks provided on the prescription or clinical chart and the receptacle or package of the pharmaceuticals. Thus, even when the medical attendant erroneously prepares the kinds and/or doses of the pharmaceuticals, the mistake can be found and alarmed, so that the mistake for medicating the erroneous kind and/or doses of the pharmaceuticals to the patient can be prevented. Furthermore, even when the medical attendant has poor knowledge and/or experiences, he can feel easy to execute the medical treatment, so that the mental burden of the medical attendant can be reduced.

Furthermore, another medication method of pharmaceuticals in accordance with the present invention is characterized by including the steps of: memorizing kinds of pharmaceuticals and information with respect to each pharmaceutical and electronic prescriptions or clinical charts, on which at least kinds and doses of pharmaceuticals to be medicated to patients are described, in a database; providing a distinguishing mark corresponding to kind and dose of pharmaceutical on a receptacle or a package thereof; reading the distinguishing mark provided on the receptacle or package of the prepared pharmaceuticals by using a recognition apparatus when the pharmaceuticals to be medicated to a patient are prepared by following the kinds and doses of the pharmaceuticals described on the electronic prescription or clinical chart; comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

That is, by such the method, the clinical chart which has conventionally been described on a paper and exchanged between the doctor and the medical attendant is formed as the electronic information and the data can be transmitted between the terminal equipments, so that the medical services can be executed effectively, further to the above-mentioned effects. Furthermore, there is no need to affix the barcodes with respect to the patient and the pharmaceuticals on the prescription or clinical chart, so that the time for identifying the patient and the pharmaceuticals can be shortened.

Furthermore, it is possible to prevent the medication mistake due to the erroneous instruction on the prescription or clinical chart by the doctor in the above-mentioned methods by further judging whether two or more pharmaceuticals are prohibited to be combined with each other when two or more pharmaceuticals has been described or will be described on the prescription or clinical chart; and stopping the medication of the pharmaceuticals when two or more pharmaceuticals are prohibited to be combined with each other.

Still furthermore, it is possible to prevent the medication mistake due to the erroneous instruction on the prescription or clinical chart by the doctor or due to the misunderstand of the medical attendant in the above-mentioned systems by providing distinguishing marks for identifying the patient on the prescription or clinical chart; identifying the patient from the distinguishing marks by using a distinguishing apparatus; accumulatively memorizing total dose of each medicated pharmaceutical with respect to each identified patient in the database; comparing the total dose of each pharmaceutical with a permissible dose thereof which is previously memorized in the database; and stopping the medication of the pharmaceuticals when the total dose surpasses the permissible dose.

Still furthermore, it is possible to prevent the medication mistake due to the erroneous instruction on the prescription or clinical chart by the doctor or due to the misunderstand of the medical attendant in the above-mentioned systems by providing distinguishing marks for identifying the patient on the prescription or clinical chart; identifying the patient from the distinguishing marks by using a distinguishing apparatus; memorizing date and time of last medication of each pharmaceutical with respect to each identified patient in the database; calculating elapsed time from the last medication with respect to each pharmaceutical; comparing the calculated elapsed time with a predetermined time during which the medication is prohibited; and stopping the medication of the pharmaceuticals when the elapsed time has not reached to the predetermined time.

Still furthermore, it is possible to prevent the medication mistake that the pharmaceuticals for another patient is erroneously medicated to different patient in the above-mentioned systems by providing a distinguishing mark on a body of the patient or in the vicinity of a bed; identifying the patient from the distinguishing mark by using a distinguishing apparatus; comparing the identified patient with the patient described on the prescription or clinical chart; and stopping the medication of the pharmaceuticals when the patients do not coincide.

What is claimed is:

1. A medication system of pharmaceuticals comprising:
   a database for memorizing kinds of pharmaceuticals and information with respect to each pharmaceutical;
   a first recognition means connected to the database and for recognizing at least the kind and dose of a pharmaceutical from a distinguishing mark provided on a receptacle or a package of each pharmaceutical;
   a second recognition means connected to the database and for recognizing at least the kind and dose of pharmaceutical from a distinguishing mark provided on a prescription or a clinical chart;
   a comparison means for comparing the kinds and doses of the pharmaceuticals recognized by the first recognition means with those recognized by the second recognition means; and
   an alarm means for outputting an alarm when at least one of the kinds and the doses of pharmaceuticals does not coincide in a result of the comparison by the comparison means.

2. The medication system of pharmaceuticals in accordance with claim 1, wherein the comparison means further judges whether two or more pharmaceuticals are prohibited to be combined with each other when two or more pharmaceuticals has been described on the prescription or clinical chart; and the alarm means outputs an alarm when two or more pharmaceuticals are prohibited to be combined with each other.

3. The medication system of pharmaceuticals in accordance with claim 1, wherein the second recognition means identifies the patient from the distinguishing marks for identifying the patient provided on the prescription or clinical chart; the first recognition means accumulatively memorizes total dose of each medicated pharmaceutical with respect to each patient identified by the second recognition means in the database; the comparison means compares the total dose of each pharmaceutical with a permissible dose thereof which is previously memorized in the database; and the alarm means outputs an alarm when the total dose surpasses the permissible dose.

4. The medication system of pharmaceuticals in accordance with claim 1, wherein the second recognition means identifies the patient from the distinguishing marks for identifying the patient provided on the prescription or clinical chart; the first recognition means memorizes date and time of last medication of each pharmaceutical with respect to each patient identified by the second recognition means in the database; the comparison means calculates elapsed time from the last medication with respect to each pharmaceutical, and compares the calculated elapsed time with a predetermined time during which the medication is prohibited; and the alarm means outputs an alarm when the elapsed time has not reached to the predetermined time.

5. The medication system of pharmaceuticals in accordance with claim 1, further comprising a third recognition means for recognizing the patient from the patient recognizing mark provided on a body of the patient or in the vicinity of a bed, and wherein the comparison means compares the patient recognized by the second recognition means with the patient recognized by the third recognition means; and the alarm means outputs an alarm when the patients do not coincide.

6. The medication system of pharmaceuticals in accordance with claim 1, wherein the database is memorized in a server connected via a network.

7. The medication system of pharmaceuticals in accordance with claim 6, wherein at least the third recognition means is a codeless terminal equipment.

8. A medication system of pharmaceuticals comprising:
   a first database for memorizing kinds of pharmaceuticals and information with respect to each pharmaceutical;
   a second database for memorizing prescriptions or clinical charts on which information with respect to kinds and doses of pharmaceuticals medicated to patients are electronically recorded;
   a first recognition means connected to the first database and for recognizing at least the kind and dose of a pharmaceutical from a distinguishing mark provided on a receptacle or a package of each pharmaceutical;

a clinical chart reading means connected to the second database, for accessing the second database based on an information for identifying a patient and for reading an inherent electronic prescription or clinical chart of the patient;

a second recognition means for recognizing at least the kind and dose of pharmaceutical from the electronic prescription or clinical chart;

a comparison means for comparing the kinds and doses of the pharmaceuticals recognized by the first recognition means with those recognized by the second recognition means; and an alarm means for outputting an alarm when at least one of the kinds and the doses of pharmaceuticals does not coincide in a result of the comparison by the comparison means.

9. The medication system of pharmaceuticals in accordance with claim 8, wherein the comparison means further judges whether two or more pharmaceuticals are prohibited to be combined with each other when two or more pharmaceuticals will be described on the prescription or clinical chart; and the alarm means outputs an alarm when two or more pharmaceuticals are prohibited to be combined with each other.

10. The medication system of pharmaceuticals in accordance with claim 8, wherein the first recognition means accumulatively memorizes total dose of each medicated pharmaceutical with respect to each patient in the second database; the comparison means compares the total dose of each pharmaceutical with a permissible dose thereof which is previously memorized in the first database; and the alarm means outputs an alarm when the total dose surpasses the permissible dose.

11. The medication system of pharmaceuticals in accordance with claim 8, wherein the first recognition means memorizes date and time of last medication of each pharmaceutical with respect to each patient in the second database; the comparison means calculates elapsed time from the last medication with respect to each pharmaceutical, and compares the calculated elapsed time with a predetermined time during which the medication is prohibited; and the alarm means outputs an alarm when the elapsed time has not reached to the predetermined time.

12. The medication system of pharmaceuticals in accordance with claim 8, further comprising a third recognition means for recognizing the patient from the patient recognizing mark provided on a body of the patient or in the vicinity of a bed, and wherein the comparison means compares the patient recognized by the second recognition means with the patient recognized by the third recognition means; and the alarm means outputs an alarm when the patients do not coincide.

13. The medication system of pharmaceuticals in accordance with claim 8, wherein the database is memorized in a server connected via a network.

14. The medication system of pharmaceuticals in accordance with claim 13, wherein at least the third recognition means is a codeless terminal equipment.

15. A medication method of pharmaceuticals characterized by including the steps of:

memorizing kinds of pharmaceuticals and information with respect to each pharmaceutical in a database;

providing a distinguishing mark corresponding to the kind and a dose of each pharmaceutical on a receptacle or a package thereof;

providing a distinguishing mark corresponding to kinds and doses of pharmaceuticals described on a prescription or a clinical chart to the prescription or clinical chart;

reading the distinguishing mark provided on the prescription or clinical chat by using a recognition apparatus when pharmaceuticals to be medicated to a patient are prepared by following the description of the prescription or clinical chart;

reading the distinguishing mark provided on the receptacle or package of the prepared pharmaceuticals by using the recognition apparatus;

comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

16. The medication method of pharmaceuticals in accordance with claim 15 further comprising the steps of judging whether two or more pharmaceuticals are prohibited to be combined with each other when two or more pharmaceuticals has been described on the prescription or clinical chart; and stopping the medication of the pharmaceuticals when two or more pharmaceuticals are prohibited to be combined with each other.

17. The medication method of pharmaceuticals in accordance with claim 15, further comprising the steps of providing distinguishing marks for identifying the patient on the prescription or clinical chart; identifying the patient from the distinguishing marks by using a distinguishing apparatus; accumulatively memorizing total dose of each medicated pharmaceutical with respect to each identified patient in the database; comparing the total dose of each pharmaceutical with a permissible dose thereof which is previously memorized in the database; and stopping the medication of the pharmaceuticals when the total dose surpasses the permissible dose.

18. The medication method of pharmaceuticals in accordance with claim 15, further comprising the steps of providing distinguishing marks for identifying the patient on the prescription or clinical chart; identifying the patient from the distinguishing marks by using a distinguishing apparatus; memorizing date and time of last medication of each pharmaceutical with respect to each identified patient in the database; calculating elapsed time from the last medication with respect to each pharmaceutical; comparing the calculated elapsed time with a predetermined time during which the medication is prohibited; and stopping the medication of the pharmaceuticals when the elapsed time has not reached to the predetermined time.

19. The medication method of pharmaceuticals in accordance with claim 15, further comprising the steps of providing a distinguishing mark on a body of the patient or in the vicinity of a bed; identifying the patient from the distinguishing mark by using a distinguishing apparatus; comparing the identified patient with the patient described on the prescription or clinical chart; and stopping the medication of the pharmaceuticals when the patients do not coincide.

20. A medication method of pharmaceuticals characterized by including the steps of:

memorizing kinds of pharmaceuticals and information with respect to each pharmaceutical and electronic prescriptions or clinical charts, on which at least kinds and doses of pharmaceuticals to be medicated to patients are described, in a database;

providing a distinguishing mark corresponding to kind and dose of pharmaceutical on a receptacle or a package thereof;

reading the distinguishing mark provided on the receptacle or package of the prepared pharmaceuticals by using a recognition apparatus when the pharmaceuticals to be medicated to a patient are prepared by following the kinds and doses of the pharmaceuticals described on the electronic prescription or clinical chart;

comparing whether at least the kinds and doses of the prepared pharmaceuticals coincide with those described on the prescription or clinical chart or not from the information recorded in the database by using the read distinguishing marks; and medicating the prepared pharmaceuticals to the patient after confirming the kinds and doses of the pharmaceuticals are coincided.

21. The medication method of pharmaceuticals in accordance with claim 20 further comprising the steps of judging whether two or more pharmaceuticals are prohibited to be combined with each other when two or more pharmaceuticals will be described on the prescription or clinical chart; and stopping the medication of the pharmaceuticals when two or more pharmaceuticals are prohibited to be combined with each other.

22. The medication method of pharmaceuticals in accordance with claim 20, further comprising the steps of accumulatively memorizing total dose of each medicated pharmaceutical with respect to each patient in the database; comparing the total dose of each pharmaceutical with a permissible dose thereof which is previously memorized in the database; and stopping the medication of the pharmaceuticals when the total dose surpasses the permissible dose.

23. The medication method of pharmaceuticals in accordance with claim 20, further comprising the steps of providing distinguishing marks for identifying the patient on the prescription or clinical chart; identifying the patient from the distinguishing marks by using a distinguishing apparatus; memorizing date and time of last medication of each pharmaceutical with respect to each identified patient in the database; calculating elapsed time from the last medication with respect to each pharmaceutical; comparing the calculated elapsed time with a predetermined time during which the medication is prohibited; and stopping the medication of the pharmaceuticals when the elapsed time as not reached to the predetermined time.

24. The medication method of pharmaceuticals in accordance with claim 20, further comprising the steps of providing a distinguishing mark on a body of the patient or in the vicinity of a bed; identifying the patient from the distinguishing mark by using a distinguishing apparatus; comparing the identified patient with the patient described on the prescription or clinical chart; and stopping the medication of the pharmaceuticals when the patients do not coincide.

* * * * *

UNITED STATES PATENT AND TRADEMARK OFFICE
CERTIFICATE OF CORRECTION

PATENT NO. : 6,670,885 B2
DATED : December 30, 2003
INVENTOR(S) : Hiroyuki Kosaka It is certified that error appears in the above-identified patent and that said Letters Patent is hereby corrected as shown below:

Title page,
Item [30], Foreign Application Priority Data, please insert:
-- [30] Foreign Application Priority Data,
      Jun. 12, 2000   (JP) ................2000-175766 --

Column 18,
Line 6, "clinical chat" should read -- clinical chart --.

Column 20,
Line 19, "time as not" should read -- time has not --.

Signed and Sealed this

Twentieth Day of July, 2004

JON W. DUDAS
*Acting Director of the United States Patent and Trademark Office*